United States Patent [19]

Flynn

[11] Patent Number: 4,933,489

[45] Date of Patent: Jun. 12, 1990

[54] PROCESS FOR THE MANUFACTURE OF 6-CHLORO-1,4-DIACETOXY-2,3-DIMETHOXYNAPHTHALENE

[75] Inventor: Daniel L. Flynn, Ann Arbor, Mich.

[73] Assignee: Warner-Lambert Company, Morris Plains, N.J.

[21] Appl. No.: 790,720

[22] Filed: Oct. 24, 1985

[51] Int. Cl.$^5$ .................. C07C 67/08; C07C 69/16
[52] U.S. Cl. ...................... 560/139; 552/297; 552/307; 568/633
[58] Field of Search ............ 260/396 R; 560/139; 568/633

[56] References Cited

U.S. PATENT DOCUMENTS 4,482,492 11/1984 Kiefer ..................... 260/396 R
4,533,554 8/1985 Terao et al. ............. 260/396 R

OTHER PUBLICATIONS

Weygand et al., Synthesis of O-Diacylbenzenes, Phthalides and Naphthoquinones, Chem. Ber., 90(9), 1884-87, 1985(1957). (Excerpts translated).
Fieser et al., J. Amer. Chem. Soc., 71, 3615 (1949).
Synthesis of o-Diacylbenzenes, Phthalides and Napthoquinones Chemische Berichte, 90 Jahrg./1957/Nr.9 pp. 1879-1895.
Chem. Abstracts, 9-30-74, vol. 81, No. 13, 77377, p. 418 paragraph 6 E.P.O. Search Report, Appln. No. 86 114 796.5.

Primary Examiner—Vivian Garner
Attorney, Agent, or Firm—Ronald A. Daignault

[57] ABSTRACT

An improved process for the manufacture of the antipsoriatic agent, 6-chloro-1,4-diacetoxy-2,3-dimethoxynaphthalene, is herein described which involves in situ Diels-Alder coupling of 2,3-dimethoxybenzo-1,4-quinone with a 3-chloro-1-alkoxy-1,3-butadiene; 1,4-elimination of the alcohol with aromatization of the chlorine-bearing ring, and acetylation.

2 Claims, No Drawings

PROCESS FOR THE MANUFACTURE OF 6-CHLORO-1,4-DIACETOXY-2,3-DIMETHOXYNAPHTHALENE

BACKGROUND OF THE INVENTION

6-Chloro-1,4-diacetoxy-2,3-dimethoxynaphthalene has been reported as a novel nonsteroidal antipsoriatic agent in U.S. Pat. No. 4,466,981 through a complex multi-step synthesis.

The present invention relates to a new and improved process for the preparation of this antipsoriatic agent which process requires only one reaction vessel and room temperature throughout the operation resulting in high yields of desired product. The present invention thus affords an efficient and inexpensive method for the commercial manufacture of 6-chloro-1,4-diacetoxy-2,3-dimethoxynaphthalene.

SUMMARY OF THE INVENTION

Accordingly, the present invention comprises a process for the manufacture of 6-chloro-1,4-diacetoxy-2,3-dimethoxynaphthalene which comprises reacting at room temperature and in an inert atmosphere and inert solvent 2,3-dimethoxybenzo-1,4-quinone with a 3-chloro-1-alkoxy-1,3-butadiene; treating the resulting intermediate with acid at room temperature, and after removing the solvent reacting the residue with acetic anhydride in the presence of an acid acceptor. Alternatively, and, if desired, the acylation may precede the acid aromatization step.

DETAILED DESCRIPTION OF THE PREFERRED EMBODIMENTS

The present invention is based on the unexpected discovery of a successful Diels-Alder coupling of 2,3-dimethoxybenzo-1,4-quinone with a 3-chloro-1-alkoxy-1,3-butadiene. The 3-chloro-1-alkoxy-1,3-butadiene as a diene, has never been reported in Diels-Alder chemistry.

Furthermore, the present Diels-Alder reaction between 2,3-dimethoxybenzo-1,4-quinone and a 3-chloro-1-alkoxy-1,3-butadiene sets the stage for the following in situ reactions:

(1) adjustment of the quinone oxidation state to the required hydroquinone oxidation state;
(2) 1,4-elimination of methanol resulting in aromatization of the chlorine-bearing ring; and
(3) the hydroquinone so formed being ready for immediate acetylation.

The present coupling requires an inert atmosphere, such as nitrogen, and is carried out at room temperature with any choice of inert solvent.

As inert solvents, preferred are chlorinated hydrocarbons and aromatic hydrocarbons, such as, for example, carbon tetrachloride, chloroform, tetrachloroethylene, trichloroethylene, dichloroethylene, benzene, xylene, chlorobenzene, 2,4-dichlorobenzene, or pyridine. Most preferred are toluene or methylene chloride.

The coupling of the 2,3-dimethoxybenzo-1,4-quinone with a 3-chloro-1-alkoxy-1,3-butadiene affords an intermediate compound of the formula

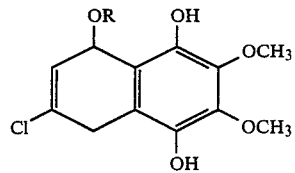

wherein R is alkyl of one to six carbon atoms, but preferably, methyl or ethyl, which compound is not isolated but immediately treated with acid in the same solvent to eliminate methanol and from a fully aromatic bicyclic ring of the formula

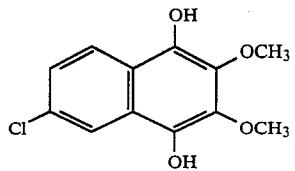

As an acid reagent, these may be used inorganic mineral acids or organic sulfonic acids, such as, for example, hydrochloric or sulfuric, methanesulfonic, p-toluenesulfonic or, preferably, dl-camphorsulfonic acid.

After removal of the solvent, the intermediate of Formula II is treated with acetic anhydride in the presence of an acid acceptor such as a base in the same reaction vessel to afford the desired product. As bases there are preferred organic amines such as tertiary amines, for example, triethylamine, but most preferred is pyridine.

Alternatively, the order of the last two steps may, if desired, be reversed so that the acylation precedes the acid elimination or aromatization step. For example, the Diels-Alder coupling reaction may be run in base, e.g., pyridine, which upon completion of the reaction to form intermediate I, said intermediate is immediately treated with acetic anhydride to form an intermediate of the formula

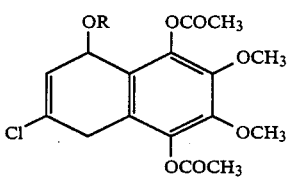

wherein R is as defined above, which following removal of base, e.g., pyridine, is treated with acid in an inert solvent, e.g., methylene chloride.

Although it is recognized that the advantage of the above reaction steps is that they are capable of being carried out in one vessel, the present invention also includes a process for manufacturing the intermediate of the Formula IIa

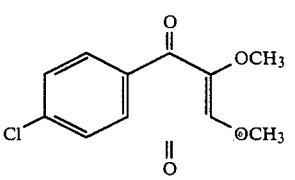

as above described by bubbling oxygen or air following the coupling reaction and passing the reaction mixture through a silica gel column or plug.

The two starting materials are known and can be prepared by known methods.

For example, 2,3-dimethoxybenzo-1,4-quinone is prepared in one step from 1,2,3-trimethoxybenzene according to the procedure described by M. Matsumoto and H. Kobayashi in *J. Org. Chem.*, 50, 1766–68 (1985). This method involves treatment of 1,2,3-trimethoxybenzene with hydrogen peroxide with a catalytic amount of potassium ferricyanide, $K_3Fe(CN)_6$, in acetic acid. Alternatively, 2,3-dimethoxybenzo-1,4-quinone is commercially available from Biochemical Labs, Gardena, Calif.

The 3-chloro-1-alkoxy-1,3-butadienes are prepared according to the procedure described by R. N. Kudyakova, S. I. Azimova, E. O. Tsetlina, and A. N. Volkov in *Zh. Org. Khim.*, 10, 949–52 (1974) by bubbling hydrogen chloride in diethyl ether at −55° C. into a vessel containing cis-1-alkoxy-1-buten-3-yne. The 1-methoxy and 1-ethoxy compounds have been specifically described.

The following nonlimiting examples illustrate the preferred methods for carrying out the process of the invention.

EXAMPLE 1

A One Pot Synthesis of 6-chloro-1,4-diacetoxy-2,3-dimethoxynaphthalene

A dichloromethane (10 ml) solution of 2,3-dimethoxybenzo-1,4-quinone (1.0 g, 5.9 mmol) and 3-chloro-1-methoxy-1,3-butadiene (1.4 g, 12.0 mmol) is stirred for 24 hours at room temperature under an inert atmosphere. After this time, 80 mg of d,1-camphorsulfonic acid is added and the solution is stirred an additional 12 hours. The mixture is then concentrated and subsequently dissolved in pyridine (15 ml) and acetic anhydride (3.0 g). After stirring for five hours under an inert atmosphere, the solution is concentrated to dryness and taken up in dichloromethane. The organics are washed with water, brine, and then dried (sodium sulfate) and concentrated to afford 1.17 g (58%) of pure 6-chloro-1,4-diacetoxy-2,3-dimethoxynaphthalene.

EXAMPLE 2

Diels-Alder Reaction for the synthesis of 2,3-dimethoxy-6-chloro-1,4-naphthoquinone A benzene (8 ml) solution of 2,3-dimethoxybenzo-1,4-quinone (1.0 g, 5.9 mmol) and 3-chloro-1-methoxy-1,3-butadiene (1.4 g, 12.0 mmol) is stirred for 35 hours under an inert atmosphere. After this time, oxygen or air is briefly bubbled through the solution (20 minutes) and the contents are passed through a silica gel plug to afford 1.07 g (72%) of analytically pure 2,3-dimethoxy-6-chloro-1,4-naphthoquinone, mp 127°–130° C.

EXAMPLE 3

A. 6-Chloro-1,4-diacetoxy-2,3-dimethoxynaphthalene

A benzene (8 ml) solution of 2,3-dimethoxybenzo-1,4-quinone (1.0 g, 5.9 mmol) and 3-chloro-1-methoxy-1,3-butadiene (1.4 g, 12.0 mmol) is stirred for 30 hours under an inert atmosphere. After this time, the reaction mixture is concentrated and then dissolved in pyridine (8 ml). Acetic anhydride (3.0 g) is added, and the solution is stirred for 12 hours under an inert atmosphere. The contents are diluted ten-fold with water and extracted with ethyl acetate. The organics are then washed with water, brine, and then dried over sodium sulfate. Concentration, followed by flash chromatography (hexane/ethyl acetate 3:1) affords 2.03 g (93%) of a compound of the formula

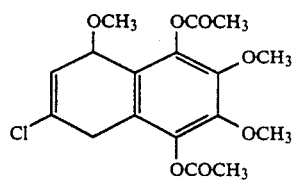

B. Alternatively the crude material before chromatography is pure enough for use in the following step A dichloromethane (1.0 ml) solution of the product obtained in A (0.10 g, 0.27 mmol) containing d,1-camphorsulfonic acid (10–20 mg) is stirred for 24 hours at room temperature. The contents are then diluted with ethyl acetate, washed with brine, and dried (sodium sulfate) to afford essentially a quantitative yield of 6-chloro-1,4-diacetoxy-2,3-dimethoxynaphthalene, mp 83°–5° C.

I claim:

1. A process for the preparation of 6-chloro-1,4-diacetoxy-2,3-dimethoxynaphthalene which comprises:
   (a) reacting 2,3-dimethoxybenzo-1,4-quinone with a 3-chloro-1-methoxy- or 3-chloro-1-ethoxy-1,3-butadiene at room temperature in an inert atmosphere and in an inert solvent;
   (b) treating the resulting intermediate with an organic sulfonic acid at room temperature;
   (c) removing the inert solvent; and
   (d) reacting the residue with acetic anhydride in the presence of an amine.

2. A process according to claim 1, wherein the inert solvent is methylene chloride or toluene; the organic sulfonic acid is methane sulfonic, p-toluenesulfonic or d1-camphorsulfonic acid, and the amine is pyridine.

* * * * *